United States Patent [19]
Yoon

[11] 3,967,625
[45] July 6, 1976

[54] DEVICE FOR STERILIZING THE HUMAN FEMALE OR MALE BY LIGATION

[76] Inventor: In Bae Yoon, 9508 Falls Bridge Lane, Potomac, Md. 20854

[22] Filed: Dec. 23, 1974

[21] Appl. No.: 535,942

Related U.S. Application Data

[62] Division of Ser. No. 383,475, July 30, 1973, Pat. No. 3,870,048.

[52] U.S. Cl............................ 128/326; 128/303 A; 128/303.1
[51] Int. Cl.².................................. A61B 17/12
[58] Field of Search............ 128/326, 303 A, 303 R, 128/4, 6, 2 B, 320, 321

[56] References Cited
UNITED STATES PATENTS

| | | | |
|---|---|---|---|
| 3,547,124 | 12/1970 | Fergusson....................... | 128/303 A |
| 3,687,138 | 8/1972 | Jarvik................................. | 128/326 |
| 3,760,810 | 9/1973 | Van Hoorn......................... | 128/326 |
| 3,820,544 | 6/1974 | Semm................................ | 128/328 |
| 3,870,048 | 3/1975 | Yoon................................. | 128/326 |
| 3,911,923 | 10/1975 | Yoon............................... | 128/303 A |

*Primary Examiner*—Aldrich F. Medbery
*Attorney, Agent, or Firm*—Stewart and Kolasch, Ltd.

[57] ABSTRACT

A method for sterilizing the human female by tubal ligation comprising the use of a ring applicator device having forceps means slidably mounted inside a cylindrical tube for grasping the Fallopian tube and pulling it within the device and means for pushing or otherwise displacing an elastic or stretchable ring over the portion of the tube held within the device, thereby effecting a ligature thereof. The procedure is preferably used in conjunction with a viewing device such as a laparoscope or a culdoscope. The placement of the elastic ring on the tubes eliminates the need for time-consuming procedures which are discomforting to the patient and the use of bulky and expensive equipment. Moreover, depending upon the size and elastic power of the rings, the sterilization can be made permanently or reversibly, as desired. The device and method are also applicable to the sterilization of the human male by the ligature of the vas.

21 Claims, 21 Drawing Figures

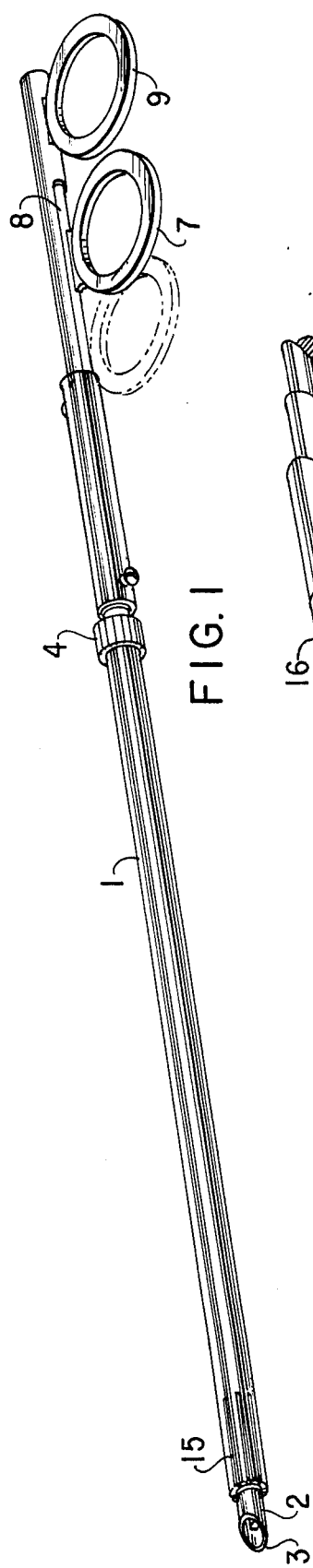
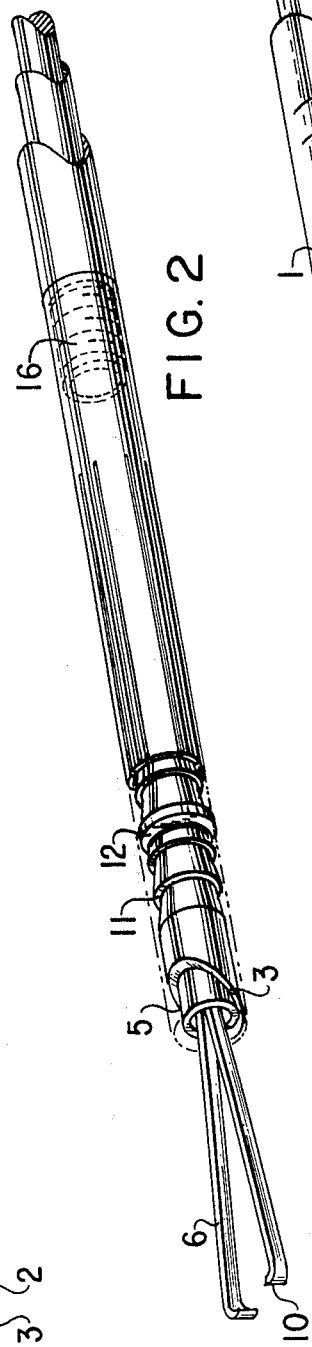
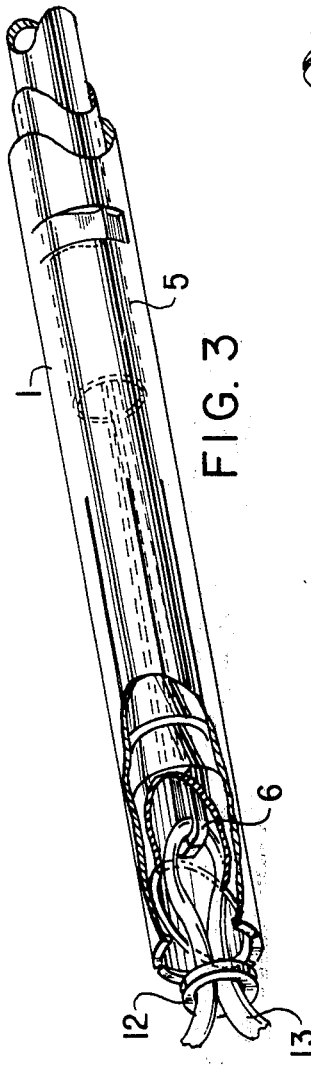
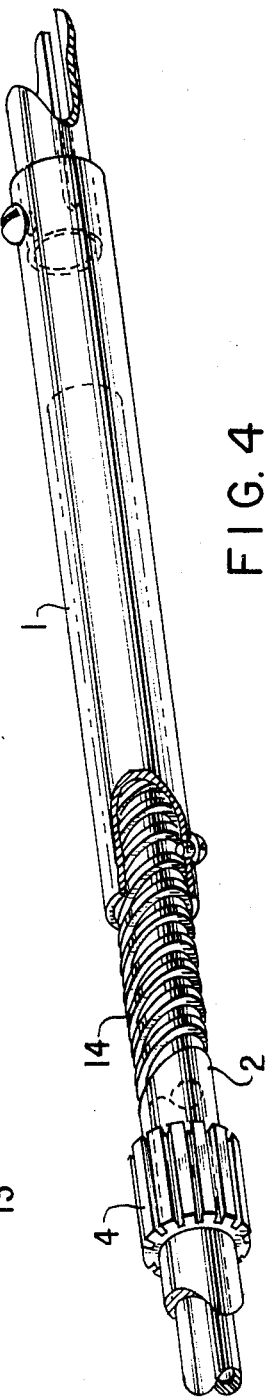
FIG. 1
FIG. 2
FIG. 3
FIG. 4

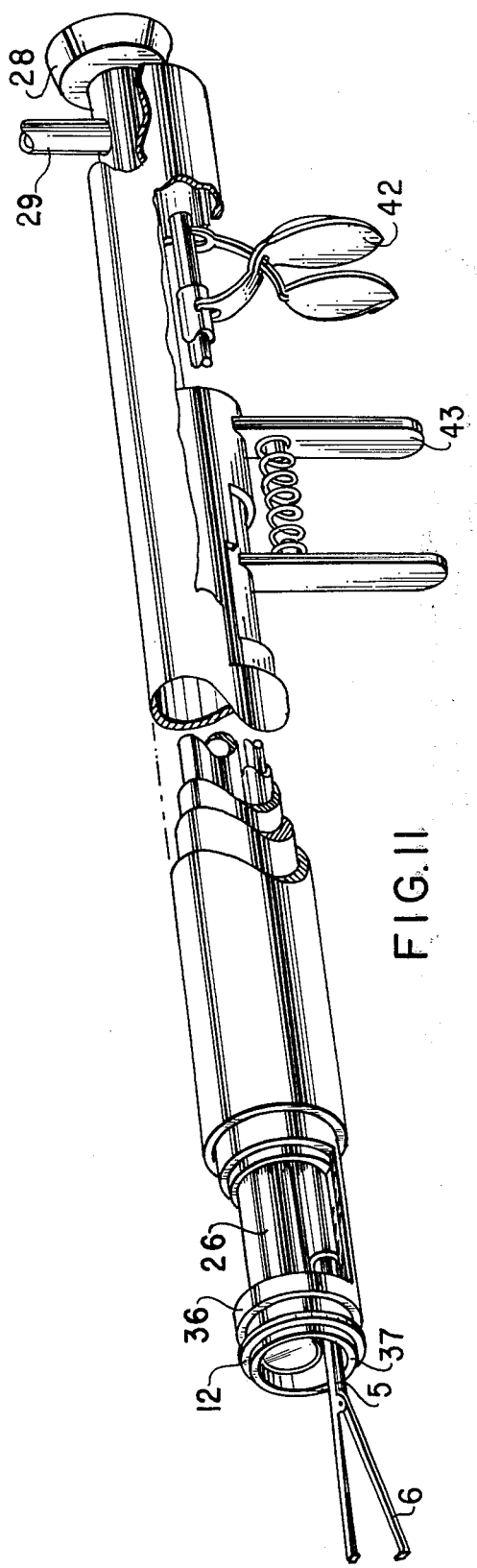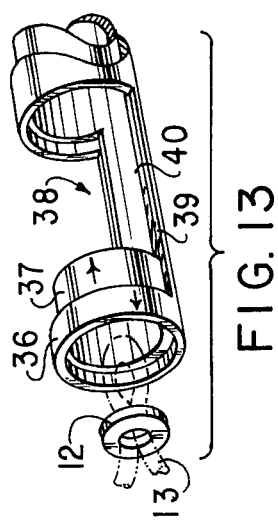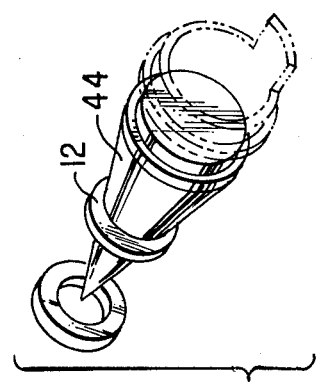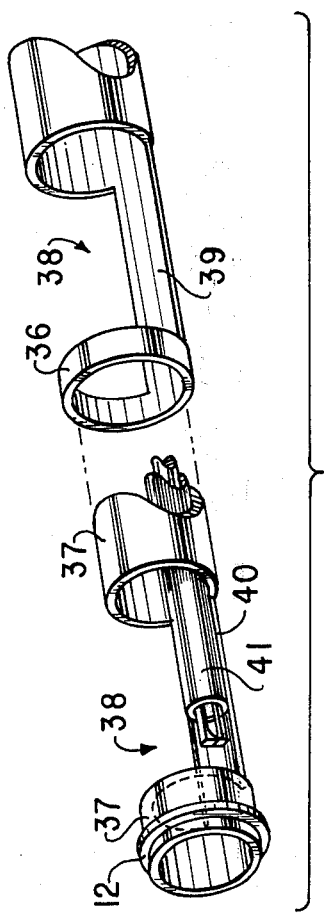
FIG. 11
FIG. 12
FIG. 13
FIG. 14

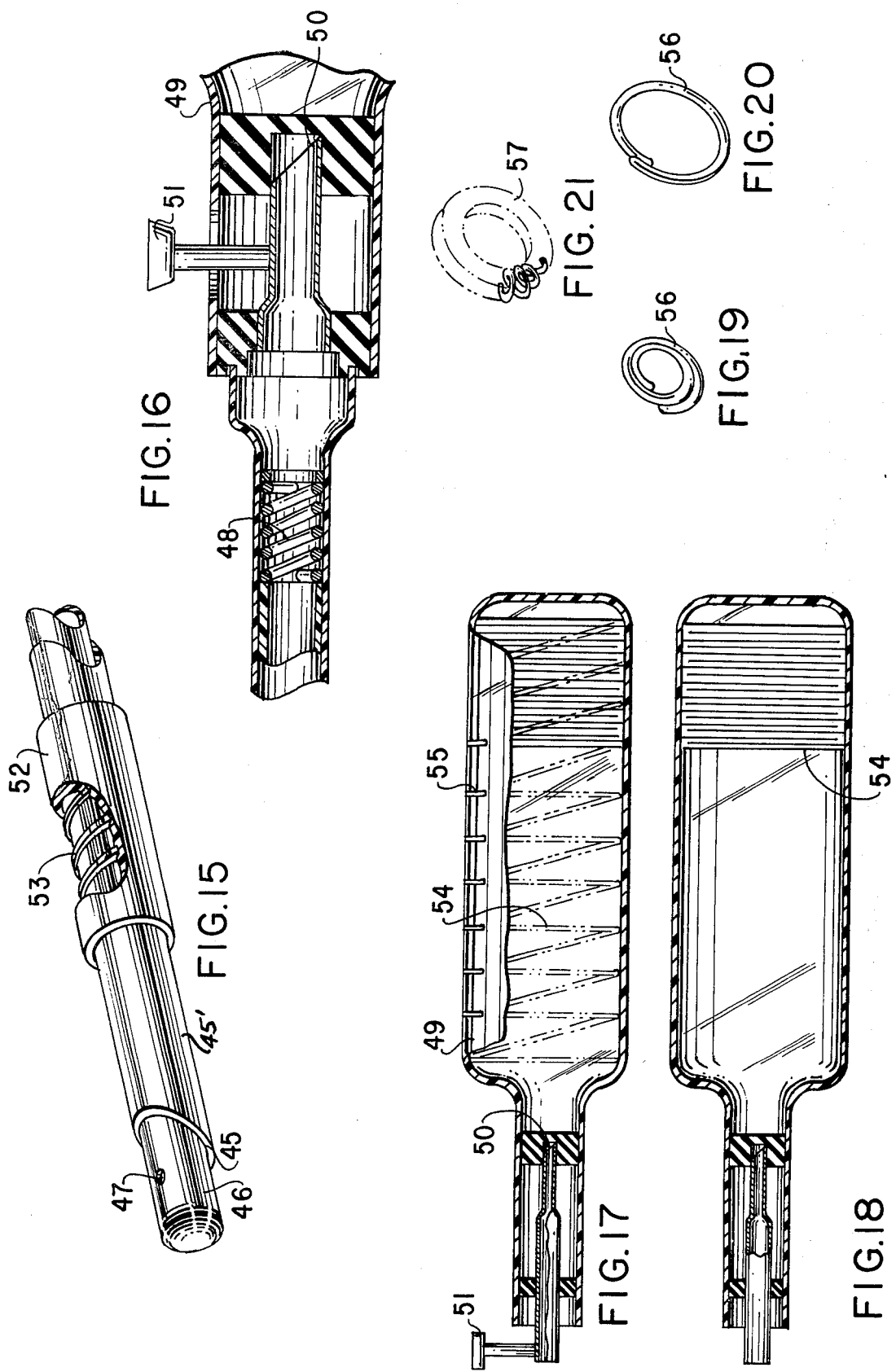

DEVICE FOR STERILIZING THE HUMAN FEMALE OR MALE BY LIGATION

This application is a divisional of copending application Ser. No. 383,475, filed on July 30, 1973 now U.S. Pat. No. 3,870,048.

BACKGROUND OF THE INVENTION

This invention relates primarily to an instrument and a method for sterilizing the human female. More particularly, it relates to a ring applicator device, combinations of said device with other instruments and a technique for carrying out tubal ligation on the human female in order to effect permanent or temporary sterilization. Moreover, the device can be used effectively to sterilize the human male.

In many areas of the world, the question of population control has become a central issue. Since birth control devices or means are not always used faithfully or fail to work in some instances, various procedures have been proposed for effecting the sterilization of women as well as men. However, many of these techniques are unpopular because of the resulting complications, the high expense and because of the general unacceptability among the populace of effecting a sterilization which is permanent and cannot be reversed. Nevertheless, sterilization is obviously an effective means for solving various problems of population explosion and of voluntarily limiting the size of the family where desired on the part of the parents. Accordingly, research into finding various techniques and instruments has continued both under private and government support.

Tubal ligation has commonly been used to effect sterilization in women. The common practice is to cut and tie the Fallopian tubes in order to prevent fertilization of the egg. More recently, the use of clips for closing the tubes has been suggested. Another recent procedure involves cauterization of the tubes by electrical means. Each of these procedures, however, involves much discomfort to the patient and highly skilled personnel to successfully complete the operation. Also, the clips have in some instances fallen off and cauterization by means of electricity involves certain dangers, such as accidental rupturing of the bowel.

SUMMARY OF THE INVENTION

One of the objects of the present invention is to provide a simplified instrument and technique for effecting permanent or temporary sterilization of the human female.

Another object of the invention is to provide a novel technique and instrument for accomplishing tubal ligation which may be employed by physicians of many degrees of skill and without the need for expensive or bulky equipment.

A further object of the invention is to provide a portable instrument for effecting tubal ligation which may be used with a minimum of discomfort to the patient.

A still further object of the invention is to provide associated equipment for use with the device of the invention.

Yet another object of the invention is to provide an instrument which can also be used for the sterilization of the human male.

These and other objects and advantages of the present invention will become apparent to those skilled in the art from a consideration of the following specification and claims, taken in conjunction with the accompanying drawings.

In accordance with the present invention, the above and other objectives are attained by the use of elastic rings for effecting the ligature of the tubes. Most preferably, the ligature is performed in conjunction with a laparoscope which is an instrument well known in the medical field for viewing the internal portions of the body. The instrument of the invention is a ring applicator which is used to quickly and effectively slip a small elastic or rubbery band around the tubes of the female in order to permanently or temporarily block the same. Basically, the instrument of the invention, shown in detail in the attached drawings, includes a grasping means which is used to pull a portion of the tube of the female into the device and slidable or rotatable tubular means for slipping or pushing the elastic or stretchable ring over the portion of the tube held in the device, thereby effecting the ligature. In operation, the entire device is inserted through the abdominal wall or by means of the vaginal route as a trocar, the grasping means is pushed forward to engage a segment of the salpinx, the grasping means is then retracted into the inner tube of the applicator device, and finally the device is manipulated so as to release the elastic ring from the end of the applicator to place it around the segment of the salpinx contained therein. Thereafter, the loop held by the elastic ring can be cut by the grasping means for permanent sterilization, if desired, or the loop can be left as is with the elastic ring therearound for permanent or temporary sterilization.

BRIEF DESCRIPTION OF THE DRAWINGS

FIGS. 1–4 show the operation of one embodiment of the ring applicator of the present invention;

FIG. 11 shows another embodiment of the ring applicator of the present invention in combination with a laparoscope;

FIG. 12 shows the front end portion of the combination shown in FIG. 11;

FIG. 13 shows how the front end portions of FIG. 11 slide with respect to each other to mount the elastic ring on the tube;

FIG. 14 shows a device for loading the elastic rings onto the end portion of a ring applicator;

FIGS. 15 and 16 show the front and rear end portions, respectively, of a device for introducing a gas into the body cavity;

FIGS. 17 and 18 disclose a further view of the rear end portion of the device of FIG. 16 where the gas cylinder is shown in the loaded and unloaded position; and FIGS. 19, 20 and 21, show enlarged views of stainless steel type rings which can be used in place of the elastic rings with the device.

DETAILED DESCRIPTION OF THE DRAWINGS

Figure 5:
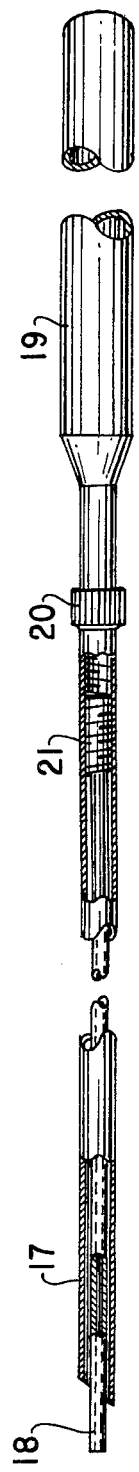
FIG. 5 discloses a needle like instrument for introducing a gas into the body cavity.

In the following description of the Figures, like elements are used throughout the various views to indicate like parts. One embodiment of the ring applicator of the present invention is shown in FIGS. 1 to 4. The device comprises an inner tube 2 disposed within an outer tube 1, said inner tube being provided with a cutting edge 3 at its front end. The outer tube is in engaging relationship with the inner tube so that by rotating the outer tube using gripping means 4 said outer tube is moved axially in the direction of the cutting edge 3. Grasping means 5 which is provided at one end with forceps 6 and at the other end with a sliding ring 7 is slidably disposed within the inner tube 2. By manually moving the sliding ring 7 the forceps 6 can be moved into and out of the inner tube 2. For example, by moving the sliding ring 7 in the direction indicated in FIG. 1 along groove 8, relating to the stationary ring 9, the forceps 6 which is compressed within tube 2, as shown in FIG. 1, is pushed out of the end portion of said tube to a position shown in FIG. 2, the arms of said forceps springing apart because of their inherent resiliency or spring-like property. If desired, the forceps means can be provided with cutting edges 10. The stationary ring 9 is provided to facilitate grasping the ring applicator and sliding the ring 7. The front end portion of tube 2 is provided with a plurality of grooves 11 which are adapted to receive elastic rings 12.

FIG. 3 shows the position of the ring applicator at a time when, for example, the tube 13 of the female is grasped by the forceps 6 and pulled inside tube 2. By turning the outer tube 1 about the external thread 14 provided on inner tube 2, the end portion 15, which can be made, for example, of spring metal, pushes the end elastic ring from the tube 2 to a position around the crimped tube 13. Then by reversing the direction of the grasping means 5, the forceps is pushed from the tube 2 which causes it to spring open, releasing the tube 13 held in a crimped condition by the elastic ring. By reversing the direction of the outer tube 1 using gripping means 4, the spring nature of the end portion 15 of said outer tube causes said portion to enlarge around the end elastic ring 12 and position itself therebehind. The device is now loaded again and in a position to discharge a second elastic ring. It is to be understood that a plurality of elastic rings may be provided in the grooves 11 of tube 2 so that one ring at a time can be used, as desired by the physician. The end portion 15 of the outer tube 1 can be attached to tube 1 by screw means 16.

FIG. 4 indicates one location in which screw threads 14 can be utilized to effect the movement of tube 1 relative to tube 2. The screw threads may, of course, be provided at any convenient location between said tubes. Also, the gripping means 4 can be provided at any convenient location.

FIG. 5 illustrates a needle instrument which is used to puncture the body cavity as the first step in the operational procedure. This instrument comprises a thin cylinder 17 which acts as a needle to puncture the skin. The needle surrounds blunted stylet 18 which functions to introduce a gas, e.g., carbon dioxide from container 19 into the abdominal cavity. Gripping means 20 is used to rotate cylinder 17 with respect to stylet 18, said stylet being provided with external threads 21. Thus, the gas is introduced into the body through the end hole in stylet 18 as it protrudes beyond the end of cylinder-needle 17.

Figure 6:
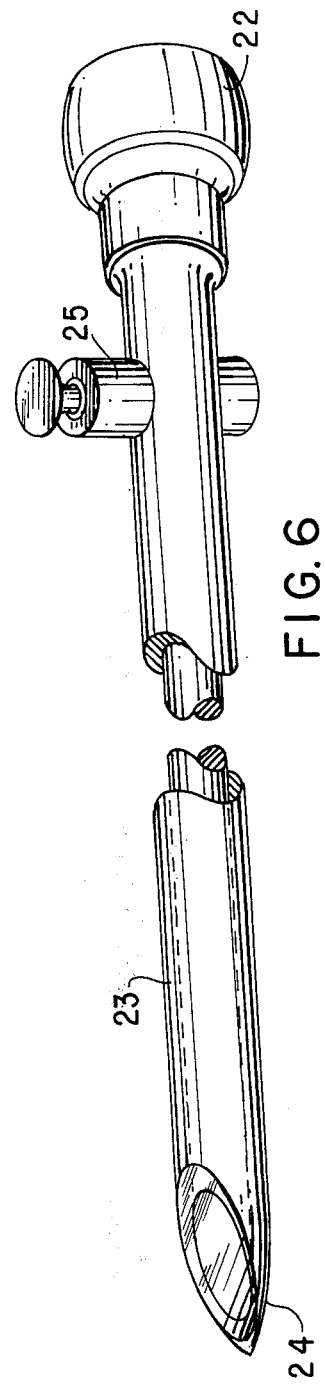
FIG. 6 shows a cannula with a trocar associated therewith to facilitate entry of the ring applicator into the body cavity.

After inflating the body cavity with carbon dioxide gas, a trocar 22, shown in FIG. 6, with a cannula 23 is introduced into the body by umbilical incision. The trocar has a pointed end 24, thereby permitting easy entry through the skin. The trocar is removed and the cannula is left in position to hold the ring applicator and/or laparoscope for use as discussed below. As can be noted in FIG. 6, the cannula is provided with a valve, e.g., a trumpet valve 25, to prevent the carbon dioxide gas from escaping.

Figure 7:
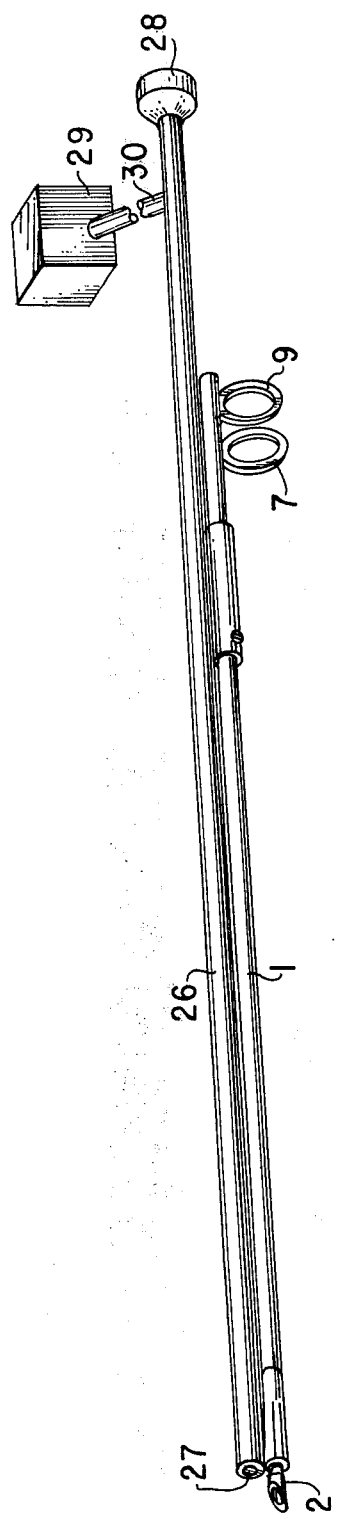
FIG. 7 shows the ring applicator of FIGS. 1 to 4 used in combination with a laparoscope.
Figure 10:
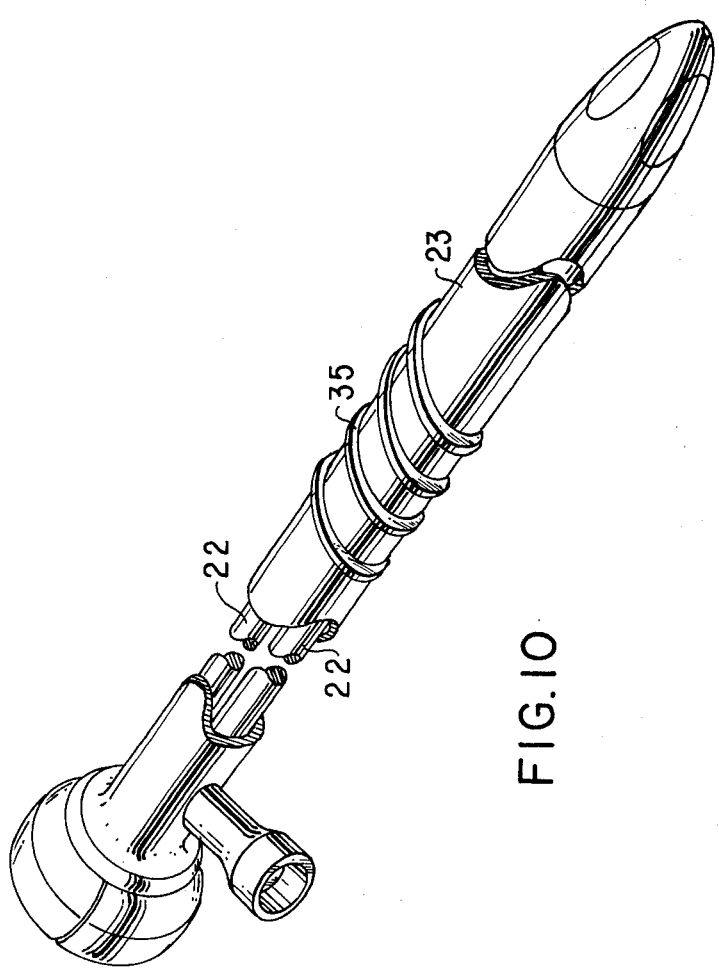
FIG. 10 discloses an embodiment in which a cannula, a laparoscope and the ring applicator can be used in an effective combination.

Laparoscopy is a well known and widely accepted technique in the medical field at the present time. The ring applicator of the present invention can be used in conjunction with a laparoscope as is schematically shown in FIG. 7, or it can be used as part of a two-hole technique using the cannula-trocar arrangement shown in FIG. 10. In FIG. 7, the ring applicator of the invention, for example, the instrument of FIG. 1, is attached to laparoscope 26. Laparoscope 26 is used to view the internal cavity during the operation by viewing through lenses 27 and 28. Light source 29 introduces a light into channel 30 to the instrument to facilitate viewing. The two instruments need not be attached, and a trocar containing two holes, as shown in FIG. 10, can be used to permit entry of the ring applicator and the laparoscope into the abdominal cavity. Alternatively, the ring applicator device of the invention can be used in conjunction with a culdoscope when entry is made through the vaginal cavity.

Figure 8:
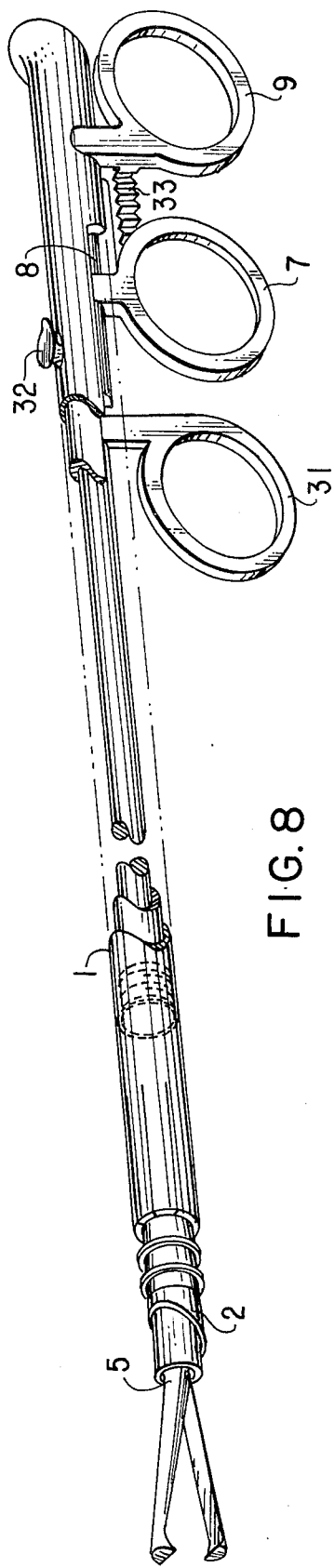
FIG. 8 shows another embodiment of the ring applicator of the present invention.

FIG. 8 shows another embodiment of the present invention wherein tubes 1 and 2 are slidably disposed with respect to each other and thus tube 2 is slid into and out of tube 1 by sliding ring 7 along groove 8. This is to be compared with the embodiment of FIG. 1 wherein screw threads are provided to enable the movement of tubes 1 and 2 with respect to each other. Also in this embodiment, ring 31 is utilized to slide grasping means 5 into and out of inner tube 2. In one feature of the present invention, a locking device 32 may be provided to lock the inner and outer tubes with respect to each other. The specific location of the locking device, as shown, facilitates locking tubes 1 and 2 together with the physician's same hand. Alternatively, a locking device in the form of a ratchet means 33 can also be used not only as an equivalent type locking device, but also to enable the axial movement of the tubes, relative to each other, in predetermined increments.

Figure 9:
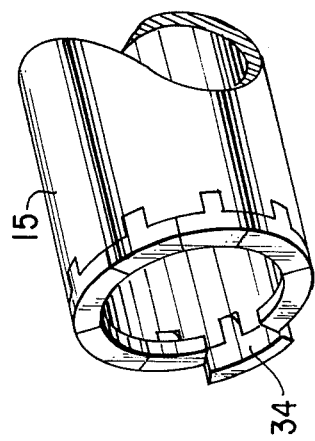
FIG. 9 shows another embodiment of the front end portion of the ring applicator which is used to eject the elastic rings from the end of said ring applicator.

FIG. 9 shows another embodiment of the front end portion 5 of the outer tube 1. Thus, said front end portion 15 can be provided with a plurality of spring-loaded sections 34 which are forced open by the elastic ring disposed on the inner tube 2 when the inner tube 2 is pulled inside the outer tube 1. Thus, for example, when the ring applicator is ready for use, the grooves 11 are loaded with elastic rings 12 and the front end portion 15 of the outer tube 1 extends over all of the elastic rings except the end ring which is to be first used during the operational procedure. By sliding inner tube 2 into outer tube 1, the elastic ring is pushed from the end of the applicator onto the crimped female tube. Then by sliding tube 2 out of tube 1, the enlarged diameter of the elastic ring disposed around the inner tube forces the spring loaded sections 34 open until said sections have reached a position between adjacent elastic rings, at which point section 34 springs closed, leaving an exposed elastic ring for next use and housing the remaining elastic rings.

FIG. 10 is similar to FIG. 6 with the exception that two trocars 22 are utilized so that multiple instruments can be used simultaneously. Also FIG. 10 shows the use of a screw-type surface 35 on the outer surface of the cannula to facilitate the introduction of the cannula into the body cavity and to prevent accidental rupturing.

FIGS. 11, 12 and 13 illustrate still another embodiment of the present invention showing a laparoscope and a ring applicator device used in combination. Also a means (not shown) can be provided for introducing a gas into the body cavity between concentric tubes. In said Figures, an inner tube 37 is slidably disposed within an outer tube 36, both of said tubes having a cutaway portion 38, so that the front and rear portions of tubes 36 and 37 are connected by saddle portions 39 and 40. Portions of tubes 36 and 37 are cutaway to provide the physician with a better overall view when looking axially through the laparoscope. An additional tube or conduit 41 is cradled in the bottom portion of the inner tube 37, said tube housing the grasping means 5 which can be moved into and out of said tube. Squeeze handles 42 operate to open and close the forceps 6. In this embodiment, one of the forceps arms is rigid and the other one is hinged with respect thereto so that the forceps can be opened and closed by the operation of said squeeze handles. Also squeeze handles 43 are associated with tubes 36 and 37 so that said tubes can be moved relative to each other, said movement pushing the elastic ring 12 from the end of tube 37 by tube 36. The embodiment of FIGS. 11, 12 and 13 is also provided with a light source 29 for the laparoscope and an air bulb or carbon dioxide source (not shown) can be associated with the instrument so that air or carbon dioxide can be introduced between concentric tubes into the body cavity.

FIG. 14 shows a cone-shaped ring applicator 44 for applying the elastic rings to the end of the tubes.

FIGS. 15 and 16 show cutaway views of the front and rear end portions respectively of a needle instrument for injecting a gas into the body cavity. The front portion shows a cutting edge 45 and a hollow rod 46 with a hole 47. The hollow rod 46 which is spring loaded by spring 48 provides communication between the body cavity and a carbon dioxide cannister 49. Thus, after the body cavity is cut or punctured by the cutting edge 45, the spring 48 pushes the hollow rod 46 into the body cavity thereby exposing hole 47 to said cavity. Then by pushing the cutting edge 50 into the carbon dioxide cannister 49, the gas is conveyed under a positive pressure from the cannister through the hole 47 into said body cavity. The cutting edge 50 can be provided with a gauge handle 51 which enables the operator to insert or retract the cutting edge in a controlled manner, thereby controlling the introduction of carbon dioxide into the body cavity.

The needle in FIG. 15 is also shown as containing a sleeve 52 which is internally threaded to receive external threads 53 provided on needle body 45'. The sleeve, which does not enter the body cavity but rather abuts against the outside of the body, e.g., the abdomen, functions to prevent the needle from being pushed into the body in an uncontrolled fashion. Thus the rod can be screwed into the body in increments in a controlled manner. This advantageous feature avoids the undesired penetration of other organs. It is apparent that such a screw arrangement can be adopted to the introduction of any instrument into the body.

FIGS. 17 and 18 show how the gas in the cannister 49 is maintained under pressure. In FIG. 17, a collapsible type baffle arrangement 54 pushes forward to assist the movement of the gas from the cannister into the needle instrument. FIG. 18 shows a cannister loaded with a gas inasmuch as the baffle means 54 is compressed against the rear portion of the cannister. Hence, a positive pressure is then present in cannister 49. The cannister can also be provided with a gauge 55 for visually determining the amount of gas which has been removed from the cannister. The cannister 49 can be made to be rechargeable by providing a valve (not shown) for reintroducing the gas therein.

FIGS. 19 and 20 show a spring stainless steel metal ring which can be used in place of the elastic rings. In FIG. 20 the ring is shown as it would appear on the ring applicator in an extended condition and FIG. 19 shows how it would appear when coiled around the female tube.

FIG. 21 shows another embodiment wherein a coiled spring 57 is used in place of the elastic ring.

In practice, the operation of the present invention is conducted as follows. First, a needle-like instrument of the type described above is inserted into the navel area in order to permit the flow of carbon dioxide or air into the abdominal cavity so as to provide more space within which to work inside the cavity. After the appropriate amount of gas has been introduced, the needle-like instrument is removed and is replaced by the trocarcannula combination. If the operation is being performed with the ring applicator of the invention being separate from the laparoscope, the single trocar is removed and replaced with said ring applicator. A laproscope is inserted into the abdominal cavity for viewing purposes at a different location. In the case where two-hole laparoscopy is being employed, a cannula containing two trocars is employed, and the ring applicator of the invention is placed into one of these holes and the laparoscope into the other of these holes. In this case, the ring applicator and the laparoscope can both be operated by the same physician.

After positioning the instruments properly within the body with the aid of the view provided by the laparoscope, the physician engages the Fallopian tube in the forceps means, pulls the tube inside of the ring applicator instrument and then slips the elastic band over the tube. The forceps means is then ejected from the instrument and the tube disengaged therefrom. If desired, two or more rings may be placed upon either or both of the tubes. The instruments are then removed, the cannula is removed and appropriate measures are used to insure that the incision or small hole in the skin area is properly cared for.

The operation is so simple, taking only about five to ten minutes, that an out-patient procedure may be employed where permitted. This is particularly important in developing countries where hospital facilities are not abundant and may not even be available. The instrument is so simple to operate that even fairly unskilled physicians can be trained to use the same quickly and effectively.

A particular advantage of the invention is that the blockage of the tubes can be made permanent or temporary, as desired. This particular feature of the invention depends upon the size and the elastic power of the rings employed. If the rings are very small and have a strong elastic power, they will so tightly grip the tubes that the blood supply in this part of the tube will be completely blocked, thereby resulting in a sloughing off of the tubes to effect a permanent sterilization, analogous to the well known method of cutting and tieing. However, if the elastic bands are of a larger size and have a smaller elastic power, it is possible to effect a temporary or reversible sterilization since, although the elastic ring will serve to prevent the ovum passage to the uterus, the holding power thereof will not be so strong as to shut off the blood supply through the tubes. Accordingly, if the woman should desire to return to a normal situation at a later time, it should be possible for the tubes to be restored to their natural function. Hence, the results of permanent or temporary sterilization are dependent upon the size of the rings used and the elastic power thereof. The technique for the operation, however, remains the same in both cases.

The rings used for application to the tubes are made of government-approved, non-tissue reactive material which have a strong enough elastic power to perform the function described herein. Various rubbery materials may, of course, be used. The preferred material is silicone rubber, for example, the material commercially available under the name "Silastic". Collagen or any other absorbable or nonabsorbable synthetic elastic material which is not harmful to human tissue may be employed, for example, latex rubber or Teflon (tetrafluoroethylene). As pointed out above, the size of the rings may be varied wherein smaller rings are used for permanent tubal ligation, and larger rings are used in connection with effecting a temporary sterilization. Spring-like metal rings, preferably made of stainless steel, can also be used, as discussed above.

The device of the invention can be made of medically-approved materials, including many different types of metals, preferably stainless steel, plastics and the like and, hence, is relatively inexpensive because of its simple nature. It can also be made as a disposable instrument, for example, from a synthetic resin such as polyethylene, polypropylene, polycarbonate, polystyrene, polyamide, polyacetates, or acrylic resin. In this embodiment, the wall of the ring applicator can itself act as a laparoscope for transmitting the light from a light source to the internal cavity, and a tube can be disposed around the inner tube (which would have a needle-like point) to push an elastic ring over the salpinx portion of the Fallopian tube when it is slid or otherwise moved with respect to said inner tube. This embodiment of the invention would be especially attractive where inexpensive instruments are a necessity. Moreover, the ring applicator device of the invention has a wide range of applicability since it can be used in conjunction with the regular abdominal laparoscopic technique, as discussed above, or in connection with the known vaginal culdoscopic procedure. The use of the device eliminates the need for large, bulky equipment which is normally used with the electrical procedures employed in the prior art as well as the complicated carbon dioxide supply systems used with other techniques. As shown in the drawings, a very simple and relatively small carbon dioxide supply system can be used together with the instrument, or a squeeze bulb may even be used to provide the necessary gas and to maintain the required gas pressure inside the abdominal cavity while the operation is being performed. The elmination of complicated electrical and gas supply systems makes it possible to save time in setting up for the procedure. In addition, as pointed out above, the operation may be carried out quite quickly in less than ten minutes.

It is to be understood that various specific mechanical embodiments may be employed to perform the various functions described herein. Basically, the invention comprises an instrument for puncturing and entering into the body cavity, grasping the Fallopian tubes, slipping an elastic ring thereover, and optionally cutting the tubes, if desired. The associated equipment represents technical modifications and adds to this basic idea, and a particularly preferred embodiment is the use of the ring applicator of the invention together with the laparoscope or a similar viewing instrument.

In an analogous manner, the method and device of the present invention may be used to effect the sterilization of the human male. In this case the appropriate incision is made and one or more elastic rings are applied to the vas to effect the ligature thereof and block the passage of the sperm. The elastic or stretchable rings used in this connection must, of course, be small enough to ligate the small diameter of the vas.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A ring applicator device for use in the sterilization of a human being which comprises an inner tube and an outer tube, said inner tube being slidably disposed within said outer tube, said inner and outer tubes having corresponding cutaway sections at their respective proximal end portions, a conduit means disposed in the lower portion of the inner tube, forceps means slidably disposed within said conduit means, means for moving said forceps means into and out of the conduit means, an optical viewing device slidably disposed within the inner tube and means for axially displacing said outer and inner tubes relative to each other, thereby removing an elastic ring from the end of said inner tube.

2. The ring applicator device of claim 1, wherein the optical viewing means is a laparoscope.

3. The ring applicator device of claim 1, wherein the optical viewing means is a culdoscope.

4. The ring applicator device of claim 1, wherein the proximal end portion of the inner tube extends beyond the proximal end portion of the outer tube, said proximal end portion of the inner tube being adapted to receive an elastic ring.

5. The ring applicator device of claim 1, wherein squeeze handles are associated with the inner and outer tubes for moving said tubes relative to each other.

6. The ring applicator device of claim 5, wherein one of said squeeze handles is attached to the inner tube, one of said squeeze handles is attached to the outer tube and a spring means connects said squeeze handles.

7. The ring applicator device of claim 1, wherein the forceps means is provided with a rigid arm and a hinged arm, and handle means are utilized for opening and closing the arms of the forceps means and sliding the forceps means into and out of the conduit means.

8. The ring applicator device of claim 7, wherein the forceps arms are provided with a cutting edge.

9. A ring applicator device for use in the sterilization of a human being which comprises an inner tube and an outer tube, said inner tube being slidably disposed within said outer tube, means for providing viewing apertures in said device comprising corresponding cut away sections in said inner and outer tubes at their respective proximal end portions, forceps means slidably disposed within said inner cylinder, and means for axially displacing said outer and inner tubes relative to each other, thereby removing an elastic ring from the end of said inner tube.

10. The ring applicator device of claim 9, wherein a conduit means is disposed within the inner tube and the forceps means is slidably disposed within said conduit means.

11. The ring applicator device of claim 9, wherein the conduit means is disposed in the lower portion of the inner tube and recessed from the proximal end of said inner tube.

12. The ring applicator device of claim 9, wherein the cut-away sections divide the inner and outer tubes into front and rear portions, said front and rear portions being connected by arc portions of the inner and outer tubes.

13. The ring applicator device of claim 9, wherein the proximal end portion of the inner tube extends beyond the proximal end portion of the outer tube, said proximal end portion of the inner tube being adapted to receive an elastic ring.

14. The ring applicator device of claim 9, wherein squeeze handles are associated with the inner and outer tubes for moving said tubes relative to each other.

15. The ring applicator device of claim 14, wherein one of said squeeze handles is attached to the inner tube, one of said squeeze handles is attached to the outer tube and a spring means connects said squeeze handles.

16. The ring applicator device of claim 9, wherein the forceps means is provided with a rigid arm and a hinged arm, and handle means are utilized for opening and closing the arms of the forceps means and sliding the forceps means into and out of the conduit means.

17. The ring applicator device of claim 9, wherein the forceps arms are provided with a cutting edge.

18. A disposable ring applicator device for use in the sterilization of a human male or female which comprises an inner tube disposed within an outer tube, the outer tube being made of a synthetic resin which is capable of transmitting light through the length thereof, grasping means slidably disposed within said inner tube, and means for moving said grasping means into and out of the inner tube, said outer tube being slidably mounted around said inner tube and functioning to displace a stretchable ring from the end of said inner tube by axially displacing the outer and inner tubes with respect to each other.

19. The device of claim 18, wherein both tubes are made of a synthetic resin which is capable of transmitting light through the length thereof.

20. The device of claim 18, wherein said inner tube is provided with a puncturing edge portion.

21. The device of claim 18, wherein a light source is combined with the ring applicator.

* * * * *